US011193145B2

(12) United States Patent
Appeldoorn et al.

(10) Patent No.: US 11,193,145 B2
(45) Date of Patent: Dec. 7, 2021

(54) ENZYME COMPOSITION

(71) Applicant: DSM IP ASSETS B.V., Heerlen (NL)

(72) Inventors: Maaike Appeldoorn, Echt (NL); Loes Elizabeth Bevers, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 17/041,954

(22) PCT Filed: Mar. 27, 2019

(86) PCT No.: PCT/EP2019/057667
§ 371 (c)(1),
(2) Date: Sep. 25, 2020

(87) PCT Pub. No.: WO2019/185680
PCT Pub. Date: Oct. 3, 2019

(65) Prior Publication Data
US 2021/0130853 A1 May 6, 2021

(30) Foreign Application Priority Data

Mar. 28, 2018 (EP) ..................................... 18164525

(51) Int. Cl.
C12P 7/10 (2006.01)
C12P 19/14 (2006.01)
C12N 9/24 (2006.01)
C12N 1/22 (2006.01)

(52) U.S. Cl.
CPC .................. *C12P 7/10* (2013.01); *C12N 1/22* (2013.01); *C12N 9/2402* (2013.01); *C12P 19/14* (2013.01); *C12P 2203/00* (2013.01)

(58) Field of Classification Search
None
See application file for complete search history.

(56) References Cited

U.S. PATENT DOCUMENTS

| 2009/0099079 A1* | 4/2009 | Emalfarb | ....... C12Y 302/01037 514/1.2 |
| 2013/0040345 A1* | 2/2013 | Los | ...................... C12N 9/2437 435/99 |
| 2021/0130853 A1* | 5/2021 | Appeldoorn | ......... C12N 9/2402 |

FOREIGN PATENT DOCUMENTS

| EP | 2886648 A1 | 6/2015 |
| JP | S62 208279 A | 9/1987 |
| WO | 2016/207144 A1 | 12/2016 |

OTHER PUBLICATIONS

De Roode, B.M. et al., "The Influence of Gluecose on the Storage and Operational Stability of Almond β-Glucosidase During the Glucosylation of Cyclohexanol", Biocatalysis and Biotransformation, Jul. 11, 2009, pp. 225-240, vol. 17.
Jain, Nishant Kumar et al., "Trehalose and Protein Stability", Current Protocols in Protein Science, Feb. 1, 2010, Unit 4.9, Supplement 59.
Sampedro, Jose G. et al., "Trehalose-enzyme interactions result in structure stabilization and activity inhibition. The role of viscosity", Molecular and Cellular Biochemistry, 2004, pp. 319-327.
Wong, Yin-How et al., "Protein stabilizing potential of simulated honey sugar cocktail under various denaturation conditions", Process Biochemistry, 2012, pp. 1933-1943, vol. 47.
Lee, James C. et al., "The Stabilization of Proteins by Sucrose", The Journal of Biological Chemistry, 1981, pp. 7193-7201, vol. 256, No. 14.
International Search Report of International Patent Application No. PCT/EP2019/057667, dated Jun. 13, 2019.

* cited by examiner

*Primary Examiner* — Richard C Ekstrom
(74) *Attorney, Agent, or Firm* — McBee Moore & Vanik IP, LLC; Susan McBee; Chester Moore

(57) ABSTRACT

The invention relates to an enzyme composition, a process for the preparation thereof and the use of the enzyme composition in enzymatic hydrolysis.

12 Claims, No Drawings

ENZYME COMPOSITION

CROSS-REFERENCE TO RELATED APPLICATIONS

This application is a National Stage entry of International Application No. PCT/EP2019/057667, filed 27 Mar. 2019, which claims priority to European Patent Application No. 18164525.0, filed 28 Mar. 2018.

BACKGROUND

Field

Herein described is an enzyme composition, a process for the preparation thereof and the use of the enzyme composition in a process for preparing a sugar product from carbohydrate material by enzymatic hydrolysis.

Description of Related Art

Lignocellulosic material is primarily composed of cellulose, hemicellulose and lignin and provides an attractive platform for generating alternative energy sources to fossil fuels. The material is available in large amounts and can be converted into valuable products e.g. sugars or biofuel, such as bioethanol.

Producing fermentation products from lignocellulosic material is known in the art and generally includes the steps of pretreatment, hydrolysis, fermentation, and optionally recovery of the fermentation products.

During the hydrolysis, which may comprise the steps of liquefaction, pre-saccharification and/or saccharification, cellulose present in the lignocellulosic material is partly (typically 30 to 95%, dependable on enzyme activity and hydrolysis conditions) converted into reducing sugars by cellulolytic enzymes. The hydrolysis typically takes place during a process lasting 6 to 168 hours (see Kumar, S., Chem. Eng. Technol. 32 (2009), 517-526) under elevated temperatures of 45 to 50° C. and non-sterile conditions.

Commonly, the sugars are then converted into valuable fermentation products such as ethanol by microorganisms like yeast. The fermentation takes place in a separate, preferably anaerobic, process step, either in the same or in a different vessel. The temperature during fermentation is adjusted to 30 to 33° C. to accommodate growth and ethanol production by microorganisms, commonly yeasts. During the fermentation process, the remaining cellulosic material is converted into reducing sugars by the enzymes already present from the hydrolysis step, while microbial biomass and ethanol are produced. The fermentation is finished once the cellulosic material is converted into fermentable sugars and all fermentable sugars are converted into ethanol, carbon dioxide and microbial biomass. This may take up to 6 days. In general, the overall process time of hydrolysis and fermentation may amount up to 13 days.

In general, cost of enzyme production is a major cost factor in the overall production process of fermentation products from lignocellulosic material (see Kumar, S., Chem. Eng. Technol. 32 (2009), 517-526). A large part of the enzyme production costs relates to the isolation and purification of enzymes, often collectively referred to as downstream processing. A typical recovery process of industrial enzymes comprises the steps of broth treatment, cell separation, concentration, purification and formulation.

Next to the optimization of the enzymes themselves, optimization of downstream processing steps such as isolation and formulation is a crucial tool to reduce overall costs of the production of sugar products and fermentation products.

For economic reasons, it is desirable to include new and innovative enzyme recovery processes aimed at reducing overall production costs in the process involving hydrolysis and fermentation of carbohydrate material.

SUMMARY

Herein provided is an improved enzyme composition, process of making the enzyme composition and use of the enzyme composition in a process for the preparation of a sugar product and/or a fermentation product from carbohydrate material. The process is improved in that the enzyme composition comprises sugar.

DETAILED DESCRIPTION

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows. The articles "a" and "an" are used herein to refer to one or to more than one (i.e. to one or at least one) of the grammatical object of the article. By way of example, "an element" may mean one element or more than one element.

In the context of the present invention, "improved" and/or "increased" is used to indicate that the presence of sugar in a cellulase, a hemicellulase and/or a pectinase enzyme composition in the amount claimed shows an advantage compared to the cellulase, hemicellulase and/or pectinase enzyme composition without sugar in the claimed amount.

Throughout the present specification and the accompanying claims, the term "sugar" is to be interpreted as a sugar or sugars. In other words, the term is to be interpreted as one type of sugar (e.g. glucose) or more than one type of sugar (e.g. a combination of glucose and xylose).

Herein described is an enzyme composition comprising (a) a cellulase, a hemicellulase and/or a pectinase and (b) sugar.

In an embodiment the enzyme composition comprises (a) a cellulase, a hemicellulase and/or a pectinase and (b) 36-272 g sugar/kg enzyme composition. So, sugar is present in the enzyme composition in an amount of 3.6-27.2% (w/w) of the enzyme composition. In an embodiment the enzyme composition as described herein comprises 36-240 g sugar/kg enzyme composition, preferably 36-200 g sugar/kg enzyme composition, more preferably 36-160 g sugar/kg enzyme composition, even more preferably 36-120 g sugar/kg enzyme composition and most preferably 36-100 g sugar/kg enzyme composition. In an embodiment the enzyme composition as described herein comprises 100-260 g sugar/g protein in the enzyme composition, preferably 108-256 g sugar/g protein in the enzyme composition, more preferably 120-252 g sugar/g protein in the enzyme composition, even more preferably 140-248 g sugar/g protein in the enzyme composition and most preferably 148-244 g sugar/g protein in the enzyme composition.

In an embodiment the enzyme composition as herein described comprises at least two types of sugar, e.g. glucose and lactose or glucose and xylose. In an embodiment the enzyme composition as herein described comprises at least three types of sugar, e.g. glucose, lactose and xylose.

In an embodiment the enzyme composition as described herein can advantageously be stored for longer periods, e.g. periods of 1 week to 1 year. In an embodiment the enzyme composition shows stability during storage. Stability during storage can be measured for example by measuring enzyme activity at the end of the storage time and compare the enzyme activity to the initial enzyme activity (i.e. at t=0). As described herein an enzyme composition as claimed still has at least 96% of its initial beta-glucosidase activity after storage for 8 weeks at room temperature or at least 92% of its initial beta-glucosidase activity after storage for 14 weeks at room temperature. The beta-glucosidase activity can be measured at 37° C. and pH 4.4 using para-nitrophenyl-β-D-glucopyranoside (pNP-BDG) as substrate. The beta-glucosidase activity assay as used herein has been described in detail in the example section.

In an embodiment the enzyme composition as described herein has a pH of 2.0 to 5.5. Preferably, the enzyme composition has a pH of 2.5 to 5.0. More preferably, the enzyme composition has a pH of 3.0 to 4.5.

The enzyme composition as described herein can be produced by multiple ways. In an embodiment sugar is added to a cellulase, a hemicellulase and/or a pectinase comprising enzyme composition. So, after production of the cellulase, hemicellulase and/or pectinase comprising enzyme composition sugar is added in the respective amount. In another embodiment the amount of sugar as described herein could be present in for example the culture medium of the microorganism that is responsible for producing the cellulase, hemicellulase and/or pectinase comprising enzyme composition. In yet another embodiment sugar is present in for example the culture medium of the microorganism that is responsible for producing the cellulase, hemicellulase and/or pectinase comprising enzyme composition in a lower amount than the amount as described herein and during recovery of the cellulase, hemicellulase and/or pectinase the enzyme composition is subjected to a concentration step (e.g. centrfigation, filtration, etc) and as a result thereof the sugar concentration reaches the range as described herein.

In an embodiment the sugar is selected from the group consisting of glucose, lactose, xylose, trehalose, sucrose, fructose, galactose, maltose, arabinose, mannose, dextran, starch, cellulose and any combination thereof. Combinations of sugars have been described herein, but other combinations are possible too. In a preferred embodiment sugar at least comprises glucose.

In an embodiment the cellulase, hemicellulase and/or pectinase is a fungal cellulase, a fungal hemicellulase and/or a fungal pectinase. In an embodiment the cellulase, hemicellulase and/or pectinase is derived from a filamentous fungus such as *Acremonium, Agaricus, Aspergillus, Aureobasidium, Beauvaria, Cephalosporium, Ceriporiopsis, Chaetomium paecilomyces, Chrysosporium, Claviceps, Cochiobolus, Coprinus, Cryptococcus, Cyathus, Emericella, Endothia, Endothia mucor, Filibasidium, Fusarium, Geosmithia, Gilocladium, Humicola, Magnaporthe, Mucor, Myceliophthora, Myrothecium, Neocaffimastix, Neurospora, Paecilomyces, Penicillium, Piromyces, Panerochaete, Pleurotus, Podospora, Pyricularia, Rasamsonia, Rhizomucor, Rhizopus, Scylatidium, Schizophyllum, Stagonospora, Talaromyces, Thermoascus, Thermomyces, Thielavia, Tolypocladium, Trametes pleurotus, Trichoderma* and *Trichophyton*. In an embodiment the filamentous fungus is *Rasamsonia*, with *Rasamsonia emersonii* being most preferred.

"Filamentous fungi" include all filamentous forms of the subdivision *Eumycota* and *Oomycota* (as defined by Hawksworth et al., In, Ainsworth and Bisby's Dictionary of The Fungi, 8th edition, 1995, CAB International, University Press, Cambridge, UK). Several strains of filamentous fungi are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL). Examples of such strains include *Aspergillus niger* CBS 513.88, *Aspergillus oryzae* ATCC 20423, IFO 4177, ATCC 1011, ATCC 9576, ATCC14488-14491, ATCC 11601, ATCC12892, *P. chrysogenum* CBS 455.95, *Penicillium citrinum* ATCC 38065, *Penicillium chrysogenum* P2, *Talaromyces emersonii* CBS 393.64, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* C1, Garg 27K, VKM F-3500-D, ATCC44006 and derivatives thereof.

*Rasamsonia* is a new genus comprising thermotolerant and thermophilic *Talaromyces* and *Geosmithia* species (J. Houbraken et al., vida supra). Based on phenotypic, physiological and molecular data, Houbraken et al. proposed to transfer the species *Talaromyces emersonii, Talaromyces byssochlamydoides, Talaromyces eburneus, Geosmithia argillacea* and *Geosmithia cylindrospora* to *Rasamsonia* gen. nov. Preferred fungi are *Rasamsonia byssochlamydoides, Rasamsonia emersonii, Thermomyces lenuginosus, Talaromyces thermophilus, Thermoascus crustaceus, Thermoascus thermophilus* and *Thermoascus aurantiacus*, with *Rasamsonia emersonii* being most preferred. *Talaromyces emersonii, Penicillium geosmithia emersonii* and *Rasamsonia emersonii* are used interchangeably herein.

In an embodiment the enzyme composition as described herein has carbohydrate material degrading and/or carbohydrate hydrolysing activity. In other words, the enzyme composition that is produced by the fungus has carbohydrate material degrading and/or carbohydrate hydrolysing activity. In other words, the enzyme composition is a cellulolytic and/or hemicellulolytic enzyme composition.

"Fungal cellulase, fungal hemicellulase and/or fungal pectinase" as used herein means a cellulase, a hemicellulase and/or a pectinase that is produced by a fungus. The cellulase, hemicellulase and/or pectinase can be native or non-native to the fungus. Examples of non-native enzymes are enzymes that are heterologous to a fungus. The term "heterologous" as used herein refers to an enzyme that is not naturally occurring in the fungus. It may be a variant of a native enzyme, an enzyme of another species or even a synthetic enzyme (e.g. computer-designed enzyme). For example, an enzyme of *Rasamsonia*, when expressed by *Aspergillus*, is considered to be heterologous. An enzyme of *Rasamsonia emersonii*, when expressed by *Rasamsonia byssochlamydoides*, is also considered to be heterologous. An enzyme of a specific *Rasamsonia emersonii* strain when expressed by another *Rasamsonia emersonii* strain is however considered to be native. When a synthetic gene is introduced into a strain and this gene encodes for an enzyme that is identical to the native enzyme found in the strain, the enzyme encoded by the synthetic gene is also considered to be native. In an embodiment the fungus is overexpressing the cellulase, hemicellulase and/or pectinase. The fungus may comprise more than one copy of a polynucleotide encoding the native or heterologous cellulase, hemicellulase and/or pectinase.

In an embodiment the enzyme composition as described herein comprises at least two cellulases and/or at least two hemicellulases. In an embodiment the enzyme composition as described herein comprises two or more, for example, three, four, five, six, seven, eight, nine or even more enzymes. The at least two cellulases may contain the same or different activities.

In an embodiment the enzyme composition as described herein comprises a cellulase, a hemicellulase and/or a pectinase selected from the group consisting of an endoglucanase, a beta-glucosidase, a lytic polysaccharide monooxygenase, a beta-xylosidase, an endoxylanase, a cellobiohydrolase and any combination thereof. In a preferred embodiment the enzyme composition as described herein comprises an endoglucanase, a beta-glucosidase, a lytic polysaccharide monooxygenase, a beta-xylosidase, an endoxylanase, a cellobiohydrolase I and a cellobiohydrolase II.

As used herein, a beta-glucosidase (EC 3.2.1.21) is any polypeptide which is capable of catalysing the hydrolysis of terminal, non-reducing β-D-glucose residues with release of β-D-glucose. Such a polypeptide may have a wide specificity for β-D-glucosides and may also hydrolyze one or more of the following: a β-D-galactoside, an α-L-arabinoside, a β-D-xyloside or a β-D-fucoside. This enzyme may also be referred to as amygdalase, β-D-glucoside glucohydrolase, cellobiase or gentobiase.

In an embodiment an enzyme composition as described herein comprises a beta-glucosidase from *Aspergillus*, such as *Aspergillus oryzae*, such as the one disclosed in WO 02/095014 or the fusion protein having beta-glucosidase activity disclosed in WO 2008/057637, or *Aspergillus fumigatus*, such as the one disclosed as SEQ ID NO:2 in WO 2005/047499 or SEQ ID NO:5 in WO 2014/130812 or an *Aspergillus fumigatus* beta-glucosidase variant, such as one disclosed in WO 2012/044915, such as one with the following substitutions: F100D, S283G, N456E, F512Y (using SEQ ID NO: 5 in WO 2014/130812 for numbering), or *Aspergillus aculeatus, Aspergillus niger* or *Aspergillus kawachi*. In another embodiment the beta-glucosidase is derived from *Penicillium*, such as *Penicillium brasilianum* disclosed as SEQ ID NO:2 in WO 2007/019442, or from *Trichoderma*, such as *Trichoderma reesei*, such as ones described in U.S. Pat. Nos. 6,022,725, 6,982,159, 7,045,332, 7,005,289, US 2006/0258554 US 2004/0102619. In an embodiment a bacterial beta-glucosidase can be used. In another embodiment the beta-glucosidase is derived from *Thielavia terrestris* (WO 2011/035029) or *Trichophaea saccata* (WO 2007/019442). In a preferred embodiment the enzyme composition comprises a beta-glucosidase from *Rasamsonia*, such as *Rasamsonia emersonii* (see WO 2012/000886).

As used herein, endoglucanases are enzymes which are capable of catalyzing the endohydrolysis of 1,4-β-D-glucosidic linkages in cellulose, lichenin or cereal β-D-glucans. They belong to EC 3.2.1.4 and may also be capable of hydrolyzing 1,4-linkages in β-D-glucans also containing 1,3-linkages. Endoglucanases may also be referred to as cellulases, avicelases, β-1,4-endoglucan hydrolases, β-1,4-glucanases, carboxymethyl cellulases, celludextrinases, endo-1,4-β-D-glucanases, endo-1,4-β-D-glucanohydrolases or endo-1,4-β-glucanases.

In an embodiment the endoglucanase comprises a GH5 endoglucanase and/or a GH7 endoglucanase. This means that at least one of the endoglucanases in the enzyme composition is a GH5 endoglucanase or a GH7 endoglucanase. In case there are more endoglucanases in the enzyme composition, these endoglucanases can be GH5 endoglucanases, GH7 endoglucanases or a combination of GH5 endoglucanases and GH7 endoglucanases. In a preferred embodiment the endoglucanase comprises a GH5 endoglucanase.

In an embodiment an enzyme composition as described herein comprises an endoglucanase from *Trichoderma*, such as *Trichoderma reesei*; from *Humicola*, such as a strain of *Humicola insolens*; from *Aspergillus*, such as *Aspergillus aculeatus* or *Aspergillus kawachii*; from *Erwinia*, such as *Erwinia carotovara*; from *Fusarium*, such as *Fusarium oxysporum*; from *Thielavia*, such as *Thielavia terrestris*; from *Humicola*, such as *Humicola grisea* var. *thermoidea* or *Humicola insolens*; from *Melanocarpus*, such as *Melanocarpus albomyces*; from *Neurospora*, such as *Neurospora crassa*; from *Myceliophthora*, such as *Myceliophthora thermophila*; from *Cladorrhinum*, such as *Cladorrhinum foecundissimum*; and/or from *Chrysosporium*, such as a strain of *Chrysosporium lucknowense*. In a preferred embodiment the endoglucanase is from *Rasamsonia*, such as a strain of *Rasamsonia emersonii* (see WO 01/70998). In an embodiment a bacterial endoglucanase can be used including, but are not limited to, *Acidothermus cellulolyticus* endoglucanase (see WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (see WO 05/093050); and *Thermobifida fusca* endoglucanase V (see WO 05/093050).

As used herein, a cellobiohydrolase (EC 3.2.1.91) is any polypeptide which is capable of catalyzing the hydrolysis of 1,4-β-D-glucosidic linkages in cellulose or cellotetraose, releasing cellobiose from the ends of the chains. This enzyme may also be referred to as cellulase 1,4-β-cellobiosidase, 1,4-β-cellobiohydrolase, 1,4-β-D-glucan cellobiohydrolase, avicelase, exo-1,4-β-D-glucanase, exocellobiohydrolase or exoglucanase.

In an embodiment an enzyme composition as described herein comprises a cellobiohydrolase I from *Aspergillus*, such as *Aspergillus fumigatus*, such as the Cel7A CBH I disclosed in SEQ ID NO:6 in WO 2011/057140 or SEQ ID NO:6 in WO 2014/130812; from *Trichoderma*, such as *Trichoderma reesei*; from *Chaetomium*, such as *Chaetomium thermophilum*; from *Talaromyces*, such as *Talaromyces leycettanus* or from *Penicillium*, such as *Penicillium emersonii*. In a preferred embodiment the enzyme composition comprises a cellobiohydrolase I from *Rasamsonia*, such as *Rasamsonia emersonii* (see WO 2010/122141).

In an embodiment an enzyme composition as described herein comprises a cellobiohydrolase II from *Aspergillus*, such as *Aspergillus fumigatus*, such as the one in SEQ ID NO:7 in WO 2014/130812 or from *Trichoderma*, such as *Trichoderma reesei*, or from *Talaromyces*, such as *Talaromyces leycettanus*, or from *Thielavia*, such as *Thielavia terrestris*, such as cellobiohydrolase II CEL6A from *Thielavia terrestris*. In a preferred embodiment the enzyme composition comprises a cellobiohydrolase II from *Rasamsonia*, such as *Rasamsonia emersonii* (see WO 2011/098580).

As used herein, lytic polysaccharide monooxygenases are enzymes that have recently been classified by CAZy in family AA9 (Auxiliary Activity Family 9) or family AA10 (Auxiliary Activity Family 10). Ergo, there exist AA9 lytic polysaccharide monooxygenases and AA10 lytic polysaccharide monooxygenases. Lytic polysaccharide monooxygenases are able to open a crystalline glucan structure and enhance the action of cellulases on lignocellulose substrates. They are enzymes having cellulolytic enhancing activity. Lytic polysaccharide monooxygenases may also affect cello-oligosaccharides. According to the latest literature, (see Isaksen et al., Journal of Biological Chemistry, vol. 289, no. 5, p. 2632-2642), proteins named GH61 (glycoside hydrolase family 61 or sometimes referred to EGIV) are lytic polysaccharide monooxygenases. GH61 was originally classified as endoglucanase based on measurement of very weak endo-1,4-β-d-glucanase activity in one family member, but have recently been reclassified by CAZy in family AA9. CBM33 (family 33 carbohydrate-binding module) is also a lytic polysaccharide monooxygenase (see Isaksen et al, Journal of Biological Chemistry, vol. 289, no. 5, pp. 2632-2642). CAZy has recently reclassified CBM33 in the AA10 family.

In an embodiment the lytic polysaccharide monooxygenase comprises an AA9 lytic polysaccharide monooxygenase. This means that at least one of the lytic polysaccharide monooxygenases in the enzyme composition and/or at least one of the additional lytic polysaccharide monooxygenases is an AA9 lytic polysaccharide monooxygenase. In an embodiment, all lytic polysaccharide monooxygenases in the enzyme composition and/or all additional lytic polysaccharide monooxygenases are AA9 lytic polysaccharide monooxygenase.

In an embodiment the enzyme composition comprises a lytic polysaccharide monooxygenase from *Thermoascus*, such as *Thermoascus aurantiacus*, such as the one described in WO 2005/074656 as SEQ ID NO:2 and SEQ ID NO:1 in WO2014/130812 and in WO 2010/065830; or from *Thielavia*, such as *Thielavia terrestris*, such as the one described in WO 2005/074647 as SEQ ID NO: 8 or SEQ ID NO:4 in WO2014/130812 and in WO 2008/148131, and WO 2011/035027; or from *Aspergillus*, such as *Aspergillus fumigatus*, such as the one described in WO 2010/138754 as SEQ ID NO:2 or SEQ ID NO: 3 in WO2014/130812; or from *Penicillium*, such as *Penicillium emersonii*, such as the one disclosed as SEQ ID NO:2 in WO 2011/041397 or SEQ ID NO:2 in WO2014/130812. Other suitable lytic polysaccharide monooxygenases include, but are not limited to, *Trichoderma reesei* (see WO 2007/089290), *Myceliophthora thermophila* (see WO 2009/085935, WO 2009/085859, WO 2009/085864, WO 2009/085868), *Penicillium pinophilum* (see WO 2011/005867), *Thermoascus* sp. (see WO 2011/039319), and *Thermoascus crustaceous* (see WO 2011/041504). Other cellulolytic enzymes that may be comprised in the enzyme composition are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 5,457,046, 5,648,263, and 5,686,593, to name just a few. In a preferred embodiment, the lytic polysaccharide monooxygenase is from *Rasamsonia*, e.g. *Rasamsonia emersonii* (see WO 2012/000892).

As used herein, an endoxylanase (EC 3.2.1.8) is any polypeptide which is capable of catalysing the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyze 1,4 xylosidic linkages in glucuronoarabinoxylans.

In an embodiment the endoxylanase comprises a GH10 xylanase. This means that at least one of the endoxylanases in the enzyme composition is a GH10 xylanase. In an embodiment all endoxylanases in the enzyme composition are GH10 xylanases.

In an embodiment an enzyme composition as described herein comprises an endoxylanase from *Aspergillus aculeatus* (see WO 94/21785), *Aspergillus fumigatus* (see WO 2006/078256), *Penicillium pinophilum* (see WO 2011/041405), *Penicillium* sp. (see WO 2010/126772), *Thielavia terrestris* NRRL 8126 (see WO 2009/079210), *Talaromyces leycettanus*, *Thermobifida fusca*, or *Trichophaea saccata* GH10 (see WO 2011/057083). In a preferred embodiment the enzyme composition comprises an endoxylanase from *Rasamsonia*, such as *Rasamsonia emersonii* (see WO 02/24926).

As used herein, beta-xylosidases (EC 3.2.1.37) are polypeptides which are capable of catalysing the hydrolysis of 1,4-β-D-xylans, to remove successive D-xylose residues from the non-reducing termini. Beta-xylosidases may also hydrolyze xylobiose. Beta-xylosidase may also be referred to as xylan 1,4-β-xylosidase, 1,4-β-D-xylan xylohydrolase, exo-1,4-β-xylosidase or xylobiase.

In an embodiment the beta-xylosidase comprises a GH3 beta-xylosidase. This means that at least one of the beta-xylosidases in the enzyme composition is a GH3 beta-xylosidase. In an embodiment all beta-xylosidases in the enzyme composition are GH3 beta-xylosidases.

In an embodiment an enzyme composition as described herein comprises a beta-xylosidase from *Neurospora crassa*, *Aspergillus fumigatus* or *Trichoderma reesei*. In a preferred embodiment the enzyme composition comprises a beta-xylosidase from *Rasamsonia*, such as *Rasamsonia emersonii* (see WO 2014/118360).

In an embodiment the enzyme composition as described herein may also comprises one or more of the below mentioned enzymes.

As used herein, a β-(1,3)(1,4)-glucanase (EC 3.2.1.73) is any polypeptide which is capable of catalysing the hydrolysis of 1,4-β-D-glucosidic linkages in β-D-glucans containing 1,3- and 1,4-bonds. Such a polypeptide may act on lichenin and cereal β-D-glucans, but not on β-D-glucans containing only 1,3- or 1,4-bonds. This enzyme may also be referred to as licheninase, 1,3-1,4-β-D-glucan 4-glucanohydrolase, β-glucanase, endo-β-1,3-1,4 glucanase, lichenase or mixed linkage β-glucanase. An alternative for this type of enzyme is EC 3.2.1.6, which is described as endo-1,3(4)-beta-glucanase. This type of enzyme hydrolyses 1,3- or 1,4-linkages in beta-D-glucanse when the glucose residue whose reducing group is involved in the linkage to be hydrolysed is itself substituted at C-3. Alternative names include endo-1,3-beta-glucanase, laminarinase, 1,3-(1,3;1,4)-beta-D-glucan 3 (4) glucanohydrolase. Substrates include laminarin, lichenin and cereal beta-D-glucans.

As used herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase. Examples of arabinofuranosidases that may be comprised in the enzyme composition include, but are not limited to, arabinofuranosidases from *Aspergillus niger, Humicola insolens* DSM 1800 (see WO 2006/114094 and WO 2009/073383) and *M. giganteus* (see WO 2006/114094).

As used herein, an α-D-glucuronidase (EC 3.2.1.139) is any polypeptide which is capable of catalysing a reaction of the following form: alpha-D-glucuronoside+H(2)O=an alcohol+D-glucuronate. This enzyme may also be referred to as alpha-glucuronidase or alpha-glucosiduronase. These enzymes may also hydrolyse 4-O-methylated glucuronic acid, which can also be present as a substituent in xylans. An alternative is EC 3.2.1.131: xylan alpha-1,2-glucuronosidase, which catalyses the hydrolysis of alpha-1,2-(4-O-methyl)glucuronosyl links. Examples of alpha-glucuronidases that may be comprised in the enzyme composition include, but are not limited to, alpha-glucuronidases from *Aspergillus clavatus, Aspergillus fumigatus, Aspergillus niger, Aspergillus terreus, Humicola insolens* (see WO 2010/014706), *Penicillium aurantiogriseum* (see WO 2009/068565) and *Trichoderma reesei*.

As used herein, an acetyl-xylan esterase (EC 3.1.1.72) is any polypeptide which is capable of catalysing the deacetylation of xylans and xylo-oligosaccharides. Such a polypeptide may catalyze the hydrolysis of acetyl groups from polymeric xylan, acetylated xylose, acetylated glucose, alpha-napthyl acetate or p-nitrophenyl acetate but, typically, not from triacetylglycerol. Such a polypeptide typically does not act on acetylated mannan or pectin. Examples of acetylxylan esterases that may be comprised in the enzyme composition include, but are not limited to, acetylxylan esterases from *Aspergillus aculeatus* (see WO 2010/108918), *Chaetomium globosum, Chaetomium gracile, Humicola insolens* DSM 1800 (see WO 2009/073709), *Hypocrea jecorina* (see WO 2005/001036), *Myceliophtera thermophila* (see WO 2010/014880), *Neurospora crassa, Phaeosphaeria nodorum* and *Thielavia terrestris* NRRL 8126 (see WO 2009/042846). In a preferred embodiment the enzyme composition comprises an acetyl xylan esterase from *Rasamsonia*, such as *Rasamsonia emersonii* (see WO 2010/000888)

As used herein, a feruloyl esterase (EC 3.1.1.73) is any polypeptide which is capable of catalysing a reaction of the form: feruloyl-saccharide+H$_2$O=ferulate+saccharide. The saccharide may be, for example, an oligosaccharide or a polysaccharide. It may typically catalyse the hydrolysis of the 4-hydroxy-3-methoxycinnamoyl (feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin. Examples of feruloyl esterases (ferulic acid esterases) that may be comprised in the enzyme composition include, but are not limited to, feruloyl esterases form *Humicola insolens* DSM 1800 (see WO 2009/076122), *Neosartorya fischeri, Neurospora crassa, Penicillium aurantiogriseum* (see WO 2009/127729), and *Thielavia terrestris* (see WO 2010/053838 and WO 2010/065448).

As used herein, a coumaroyl esterase (EC 3.1.1.73) is any polypeptide which is capable of catalysing a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. This enzyme also falls within EC 3.1.1.73 so may also be referred to as a feruloyl esterase.

As used herein, an α-galactosidase (EC 3.2.1.22) is any polypeptide which is capable of catalysing the hydrolysis of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

As used herein, a β-galactosidase (EC 3.2.1.23) is any polypeptide which is capable of catalysing the hydrolysis of terminal non-reducing β-D-galactose residues in β-D-galactosides. Such a polypeptide may also be capable of hydrolyzing α-L-arabinosides. This enzyme may also be referred to as exo-(1→4)-β-D-galactanase or lactase.

As used herein, a β-mannanase (EC 3.2.1.78) is any polypeptide which is capable of catalysing the random hydrolysis of 1,4-β-D-mannosidic linkages in mannans, galactomannans and glucomannans. This enzyme may also be referred to as mannan endo-1,4-β-mannosidase or endo-1,4-mannanase.

As used herein, a β-mannosidase (EC 3.2.1.25) is any polypeptide which is capable of catalysing the hydrolysis of terminal, non-reducing β-D-mannose residues in β-D-mannosides. This enzyme may also be referred to as mannanase or mannase.

As used herein, an endo-polygalacturonase (EC 3.2.1.15) is any polypeptide which is capable of catalysing the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

As used herein, a pectin methyl esterase (EC 3.1.1.11) is any enzyme which is capable of catalysing the reaction: pectin+n H$_2$O=n methanol+pectate. The enzyme may also be known as pectinesterase, pectin demethoxylase, pectin methoxylase, pectin methylesterase, pectase, pectinoesterase or pectin pectylhydrolase.

As used herein, an endo-galactanase (EC 3.2.1.89) is any enzyme capable of catalysing the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

As used herein, a pectin acetyl esterase is defined herein as any enzyme which has an acetyl esterase activity which catalyses the deacetylation of the acetyl groups at the hydroxyl groups of GalUA residues of pectin.

As used herein, an endo-pectin lyase (EC 4.2.2.10) is any enzyme capable of catalysing the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

As used herein, a pectate lyase (EC 4.2.2.2) is any enzyme capable of catalysing the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

As used herein, an alpha rhamnosidase (EC 3.2.1.40) is any polypeptide which is capable of catalysing the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

As used herein, exo-galacturonase (EC 3.2.1.82) is any polypeptide capable of hydrolysis of pectic acid from the non-reducing end, releasing digalacturonate. The enzyme may also be known as exo-poly-α-galacturonosidase, exopolygalacturonosidase or exopolygalacturanosidase.

As used herein, exo-galacturonase (EC 3.2.1.67) is any polypeptide capable of catalysing: $(1,4-\alpha$-D-galacturonide$)_n$+H$_2$O=$(1,4-\alpha$-D-galacturonide$)_{n-1}$+D-galacturonate. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

As used herein, exopolygalacturonate lyase (EC 4.2.2.9) is any polypeptide capable of catalysing eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

As used herein, rhamnogalacturonan hydrolase is any polypeptide which is capable of hydrolyzing the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

As used herein, rhamnogalacturonan lyase is any polypeptide which is any polypeptide which is capable of cleaving α-L-Rhap-(1→4)-α-D-GalpA linkages in an endo-fashion in rhamnogalacturonan by beta-elimination.

As used herein, rhamnogalacturonan acetyl esterase is any polypeptide which catalyzes the deacetylation of the backbone of alternating rhamnose and galacturonic acid residues in rhamnogalacturonan.

As used herein, rhamnogalacturonan galacturonohydrolase is any polypeptide which is capable of hydrolyzing galacturonic acid from the non-reducing end of strictly alternating rhamnogalacturonan structures in an exo-fashion.

As used herein, xylogalacturonase is any polypeptide which acts on xylogalacturonan by cleaving the β-xylose substituted galacturonic acid backbone in an endo-manner. This enzyme may also be known as xylogalacturonan hydrolase.

As used herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

As used herein, endo-arabinanase (EC 3.2.1.99) is any polypeptide which is capable of catalysing endohydrolysis of 1,5-α-arabinofuranosidic linkages in 1,5-arabinans. The enzyme may also be known as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

"Protease" includes enzymes that hydrolyze peptide bonds (peptidases), as well as enzymes that hydrolyze bonds between peptides and other moieties, such as sugars (glycopeptidases). Many proteases are characterized under EC 3.4 and are suitable for use in the processes as described herein. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phosphoglycerides, lipoproteins, diacylglycerols, and the like. In plants, lipids are used as structural components to limit water loss and pathogen infection. These lipids include waxes derived from fatty acids, as well as cutin and suberin.

"Ligninase" includes enzymes that can hydrolyze or break down the structure of lignin polymers. Enzymes that can break down lignin include lignin peroxidases, manganese peroxidases, laccases and feruloyl esterases, and other enzymes described in the art known to depolymerize or otherwise break lignin polymers. Also included are enzymes capable of hydrolyzing bonds formed between hemicellulosic sugars (notably arabinose) and lignin. Ligninases include but are not limited to the following group of enzymes: lignin peroxidases (EC 1.11.1.14), manganese peroxidases (EC 1.11.1.13), laccases (EC 1.10.3.2) and feruloyl esterases (EC 3.1.1.73).

"Hexosyltransferase" (2.4.1-) includes enzymes which are capable of catalysing a transferase reaction, but which can also catalyze a hydrolysis reaction, for example of cellulose and/or cellulose degradation products. An example of a hexosyltransferase which may be used is a β-glucanosyltransferase. Such an enzyme may be able to catalyze degradation of (1,3)(1,4)glucan and/or cellulose and/or a cellulose degradation product.

"Glucuronidase" includes enzymes that catalyze the hydrolysis of a glucuronoside, for example β-glucuronoside to yield an alcohol. Many glucuronidases have been characterized and may be suitable for use, for example β-glucuronidase (EC 3.2.1.31), hyaluronoglucuronidase (EC 3.2.1.36), glucuronosyl-disulfoglucosamine glucuronidase (3.2.1.56), glycyrrhizinate β-glucuronidase (3.2.1.128) or α-D-glucuronidase (EC 3.2.1.139).

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. As described herein, an expansin-like protein or swollenin-like protein may comprise one or both of such domains and/or may disrupt the structure of cell walls (such as disrupting cellulose structure), optionally without producing detectable amounts of reducing sugars.

A cellulose induced protein, for example the polypeptide product of the cip1 or cip2 gene or similar genes (see Foreman et al., J. Biol. Chem. 278(34), 31988-31997, 2003), a cellulose/cellulosome integrating protein, for example the polypeptide product of the cipA or cipC gene, or a scaffoldin or a scaffoldin-like protein. Scaffoldins and cellulose integrating proteins are multi-functional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module (CBM) that mediates attachment of the cellulosome to its substrate. A scaffoldin or cellulose integrating protein may comprise one or both of such domains.

A catalase; the term "catalase" means a hydrogen-peroxide: hydrogen-peroxide oxidoreductase (EC 1.11.1.6 or EC 1.11.1.21) that catalyzes the conversion of two hydrogen peroxides to oxygen and two waters. Catalase activity can be determined by monitoring the degradation of hydrogen peroxide at 240 nm based on the following reaction: $2H_2O_2 \rightarrow 2H_2O+O_2$. The reaction is conducted in 50 mM phosphate pH 7.0 at 25° C. with 10.3 mM substrate ($H_2O_2$) and approximately 100 units of enzyme per ml. Absorbance is monitored spectrophotometrically within 16-24 seconds, which should correspond to an absorbance reduction from 0.45 to 0.4. One catalase activity unit can be expressed as one micromole of $H_2O_2$ degraded per minute at pH 7.0 and 25° C.

The term "amylase" as used herein means enzymes that hydrolyze alpha-1,4-glucosidic linkages in starch, both in amylose and amylopectin, such as alpha-amylase (EC 3.2.1.1), beta-amylase (EC 3.2.1.2), glucan 1,4-alpha-glucosidase (EC 3.2.1.3), glucan 1,4-alpha-maltotetraohydrolase (EC 3.2.1.60), glucan 1,4-alpha-maltohexaosidase (EC 3.2.1.98), glucan 1,4-alpha-maltotriohydrolase (EC 3.2.1.116) and glucan 1,4-alpha-maltohydrolase (EC 3.2.1.133), and enzymes that hydrolyze alpha-1,6-glucosidic linkages, being the branch-points in amylopectin, such as pullulanase (EC 3.2.1.41) and limit dextinase (EC 3.2.1.142).

In an embodiment the enzyme composition is a whole fermentation broth of a fungus, preferably of a filamentous fungus. The whole fermentation broth can be prepared from fermentation of non-recombinant and/or recombinant filamentous fungi. In an embodiment the filamentous fungus is a recombinant filamentous fungus comprising one or more genes which can be homologous or heterologous to the filamentous fungus. In an embodiment, the filamentous fungus is a recombinant filamentous fungus comprising one or more genes which can be homologous or heterologous to the filamentous fungus, wherein the one or more genes encode enzymes that can degrade a cellulosic substrate. The whole fermentation broth may comprise any of the enzymes described above or any combination thereof.

Preferably, the enzyme composition is a whole fermentation broth wherein cells are killed, i.e. nonviable. In an embodiment the enzyme composition comprises a whole fermentation broth, organic acid(s), killed cells and/or cell debris, and culture medium.

In an embodiment the enzyme composition as described herein comprises filamentous fungal cells and the ratio of nonviable filamentous fungal cells to viable filamentous fungal cells in the enzyme composition is at least 10:1. The ratio of nonviable filamentous fungal cells to viable filamentous fungal cells in the enzyme composition is at least 50:1, preferably at least 100:1, more preferably at least 500:1, even more preferably at least 1000:1, most preferably at least 10,000:1 and in particular at least 100,000:1. As used herein, the term "viable filamentous fungal cell" refers to a filamentous fungal cell that is alive and capable of regeneration and/or propagation and ability to grow, while in a vegetative, frozen, preserved, or reconstituted state. Viability is measured by plating 50 μl of an enzyme composition according to the invention and dilutions thereof on a malt extract agar plate (3% w/w malt extract, 0.3% w/w soy peptone, 1.5% w/w agar, pH 5.6) and incubating the plate at the optimal growth temperature of the filamentous fungal cells for 3 days. The amount of viable filamentous fungal cells is determined by counting colony forming units and comparison with counts of colony forming units of non-killed off broth.

Generally, the filamentous fungi are cultivated in a cell culture medium suitable for production of enzymes capable of hydrolyzing a cellulosic substrate. The cultivation takes place in a suitable nutrient medium comprising carbon and nitrogen sources and inorganic salts, using procedures known in the art. Suitable culture media, temperature ranges and other conditions suitable for growth and cellulase and/or hemicellulase and/or pectinase production are known in the art. The whole fermentation broth can be prepared by growing the filamentous fungi to stationary phase and maintaining the filamentous fungi under limiting carbon conditions for a period of time sufficient to express the one or more cellulases and/or hemicellulases and/or pectinases. Once enzymes, such as cellulases and/or hemicellulases and/or pectinases, are secreted by the filamentous fungi into the fermentation medium, the whole fermentation broth can be used. The whole fermentation broth of the present invention may comprise filamentous fungi. In some embodiments, the whole fermentation broth comprises the unfractionated contents of the fermentation materials derived at the end of the fermentation. Typically, the whole fermentation broth comprises the spent culture medium and cell debris present after the filamentous fungi are grown to saturation, incubated under carbon-limiting conditions to allow protein synthesis (particularly, expression of cellulases and/or hemicellulases and/or pectinases). In some embodiments, the whole fermentation broth comprises the spent cell culture medium, extracellular enzymes and filamentous fungi. The filamentous fungal cells present in whole fermentation broth can be killed using methods known in the art to produce a cell-killed whole fermentation broth. For instance, addition of succinic acid leads to killing of the cells. If needed, the cells may also be lysed and/or permeabilized. In an embodiment, the whole fermentation broth is a cell-killed whole fermentation broth, wherein the whole fermentation broth containing the filamentous fungal cells are killed. In other words, the whole fermentation broth comprises more nonviable cells than viable cells, preferably only nonviable cells. In some embodiments, the cells are killed by lysing the filamentous fungi by chemical and/or pH treatment to generate the cell-killed whole broth of a fermentation of the filamentous fungi. In some embodiments, the cells are killed by lysing the filamentous fungi by chemical and/or pH treatment and adjusting the pH of the cell-killed fermentation mix to a suitable pH. In an embodiment, the whole fermentation broth is mixed with succinic acid.

The term "whole fermentation broth" as used herein refers to a preparation produced by cellular fermentation that undergoes no or minimal recovery and/or purification. For example, whole fermentation broths are produced when microbial cultures are grown to saturation, incubated under carbon-limiting conditions to allow protein synthesis (e.g., expression of enzymes by host cells) and secretion into cell culture medium. Typically, the whole fermentation broth is unfractionated and comprises spent cell culture medium, extracellular enzymes, and microbial, preferably nonviable, cells. As used herein, it also may comprise 36-272 g sugar per kg whole fermentation broth.

In an embodiment the whole fermentation broth can be fractionated and the one or more of the fractionated contents can be used. For instance, the killed cells and/or cell debris can be removed from a whole fermentation broth to provide an enzyme composition that is free of these components.

The whole fermentation broth may further comprise a preservative and/or anti-microbial agent. Such preservatives and/or agents are known in the art. In an embodiment the succinic acid used for killing the cells can also have the function of preservative and/or anti-microbial agent.

The whole fermentation broth as described herein is typically a liquid, but may contain insoluble components, such as killed cells, cell debris, culture media components, and/or insoluble enzyme(s). In some embodiments, insoluble components may be removed to provide a clarified whole fermentation broth.

In an embodiment the whole fermentation broth may be supplemented with one or more enzyme activities that are not expressed endogenously, or expressed at relatively low level by the filamentous fungi, to improve the degradation of the cellulosic substrate, for example, to fermentable sugars such as glucose or xylose. The supplemental enzyme(s) can be added as a supplement to the whole fermentation broth and the enzymes may be a component of a separate whole fermentation broth, or may be purified, or minimally recovered and/or purified.

In an embodiment the whole fermentation broth may be supplemented with one or more sugars as described herein.

In an embodiment the whole fermentation broth may be supplemented with at least another whole fermentation broth. The other whole fermentation broth may be derived from the same type of fungus or from another type of fungus, e.g. a first whole fermentation broth may be derived from a first filamentous fungus, while a second whole fermentation broth may be derived from the same or another filamentous fungus.

In an embodiment the whole fermentation broth comprises a whole fermentation broth of a fermentation of a recombinant filamentous fungus overexpressing one or more enzymes to improve the degradation of a carbohydrate material. Alternatively, the whole fermentation broth can comprise a mixture of a whole fermentation broth of a fermentation of a non-recombinant filamentous fungus and a recombinant filamentous fungus overexpressing one or more enzymes to improve the degradation of a carbohydrate material. In an embodiment, the whole fermentation broth comprises a whole fermentation broth of a fermentation of a filamentous fungus overexpressing beta-glucosidase. Alternatively, the whole fermentation broth for use in the present methods and reactive compositions can comprise a mixture of a whole fermentation broth of a fermentation of a non-recombinant filamentous fungus and a whole fermentation broth of a fermentation of a recombinant filamentous fungus overexpressing a beta-glucosidase.

In an embodiment the enzyme composition as described herein is "thermostable", meaning it comprises at least a thermostable enzyme. A "thermostable" enzyme as used herein means that the enzyme has a temperature optimum of 50° C. or higher, 60° C. or higher, 70° C. or higher, 75° C. or higher, 80° C. or higher, 85° C. or higher. They may for example be isolated from thermophilic microorganisms or may be designed by the skilled person and artificially synthesized. In one embodiment the polynucleotides may be isolated or obtained from thermophilic or thermotolerant filamentous fungi or isolated from non-thermophilic or non-thermotolerant fungi, but are found to be thermostable. By "thermophilic fungus" is meant a fungus that grows at a temperature of 50° C. or higher. By "themotolerant" fungus is meant a fungus that grows at a temperature of 45° C. or higher, having a maximum near 50° C.

In an embodiment the container(s) used in the process for the preparation of an enzyme composition as described herein have a volume of at least 1 m$^3$. Preferably, the containers have a volume of at least 1 m$^3$, at least 2 m$^3$, at least 3 m$^3$, at least 4 m$^3$, at least 5 m$^3$, at least 6 m$^3$, at least 7 m$^3$, at least 8 m$^3$, at least 9 m$^3$, at least 10 m$^3$, at least 15 m$^3$, at least 20 m$^3$, at least 25 m$^3$, at least 30 m$^3$, at least 35 m$^3$, at least 40 m$^3$, at least 45 m$^3$, at least 50 m$^3$, at least 60 m$^3$, at least 70 m$^3$, at least 75 m$^3$, at least 80 m$^3$, at least 90 m$^3$. In general, the container(s) will be smaller than 300 m$^3$.

The term "culturing" refers to growing a population of microbial cells, e.g. filamentous fungal cells, under suitable conditions for growth, in a liquid or solid medium. In an embodiment the filamentous fungus is cultured in a fed-batch culture, a batch culture, a continuous culture or any combination thereof. Preferably, the filamentous fungus is cultured in a fed-batch culture. A person skilled in the art is well aware of the various modes of culturing and its conditions. In an embodiment the culturing is conducted under aerobic conditions. A person skilled in the art is well aware of fermentor designs for aerobic cultivation such as for instance stirred tanks and bubble columns.

In an embodiment the invention also relates to a kit comprising (a) a packaging and (b) an enzyme composition as described herein. As used herein, "packaging" refers to a solid matrix, material, or container customarily used in a system and capable of holding within fixed limits components of a kit as described herein. A kit also may contain instructions for use of the enzyme composition. For example, instructions may be provided for use of the enzyme composition in enzymatic hydrolysis of a carbohydrate material or instructions for use of the enzyme composition in a process for the preparation of a fermentation product, as described herein. Instructions may be provided in printed form or in the form of an electronic medium, in the form of a website address or an app where such instructions may be obtained.

The present invention also relates to a process for the preparation of a sugar product from carbohydrate material, comprising the steps of (a) enzymatically hydrolysing the carbohydrate material in one or more containers using an enzyme composition as described herein or a kit as described herein to obtain a sugar product, and (b) optionally, recovering the sugar product. The sugar product is an enzymatically hydrolysed carbohydrate material.

The present invention also relates to a process for the preparation of a fermentation product from carbohydrate material, comprising the steps of (a) performing a process for the preparation of a sugar product as described herein, (b) fermenting the sugar product to produce a fermentation product, and (c) optionally, recovering the fermentation product.

In an embodiment the pH in the enzymatic hydrolysis is between 3.0 and 6.5, preferably between 3.5 and 5.5, more preferably between 4.0 and 5.0.

During or after enzymatic hydrolysis, the carbohydrate material may be subjected to at least one solid/liquid separation. The methods and conditions of solid/liquid separation will depend on the type of carbohydrate material used and are well within the scope of the skilled artisan. Examples include, but are not limited to, centrifugation, cyclonic separation, filtration, decantation, sieving and sedimentation. In a preferred embodiment the solid/liquid separation is performed by centrifugation or sedimentation. During solid/liquid separation, means and/or aids for improving the separation may be used.

In an embodiment the carbohydrate material is subjected to a pretreatment step before the enzymatic hydrolysis. In an embodiment the carbohydrate material is subjected to a washing step before the enzymatic hydrolysis.

In the processes as described herein carbohydrate material may be added to the one or more containers. In an embodiment the enzyme composition is already present in the one or more containers before the carbohydrate material is added. In another embodiment the enzyme composition may be added to the one or more containers. In an embodiment the carbohydrate material is already present in the one or more containers before the enzyme composition is added. In an embodiment both the carbohydrate material and the enzyme composition are added simultaneously to the one or more containers. The enzyme composition present in the one or more containers may be an aqueous composition.

In an embodiment the enzymatic hydrolysis comprises at least a liquefaction step wherein the carbohydrate material is liquefied in at least a first container, and a saccharification step wherein the liquefied lignocellulosic material is hydrolysed in the at least first container and/or in at least a second container. Saccharification can be done in the same container as the liquefaction (i.e. at least first container), it can also be done in a separate container (i.e. the at least second container). So, in the enzymatic hydrolysis of the processes as described herein liquefaction and saccharification may be combined. Alternatively, the liquefaction and saccharification may be separate steps. In an embodiment the enzymatic hydrolysis comprises (a) a liquefaction step wherein the carbohydrate material is liquefied in a first container to obtain liquefied material, and (b) a saccharification step wherein the liquefied material is hydrolysed in the first container and/or in a second container.

The enzymatic hydrolysis can be performed in one or more containers, but can also be performed in one or more tubes or any other continuous system. This also holds true when the enzymatic hydrolysis comprises a liquefaction step and a saccharification step. The liquefaction step can be performed in one or more containers, but can also be performed in one or more tubes or any other continuous system and/or the saccharification step can be performed in one or more containers, but can also be performed in one or more tubes or any other continuous system. Examples of containers to be used in the present invention include, but are not limited to, fed-batch stirred containers, batch stirred containers, continuous flow stirred containers with ultrafiltration, and continuous plug-flow column reactors. Stirring can be done by one or more impellers, pumps and/or static mixers.

The enzyme composition used in the enzymatic hydrolysis may be added before and/or during the enzymatic hydrolysis. As indicated above, when the lignocellulosic material is subjected to a solid/liquid separation before enzymatic hydrolysis, the enzymes used in the enzymatic hydrolysis may be added before the solid/liquid separation. Alternatively, they may also be added after solid/liquid separation or before and after solid/liquid separation. The enzyme composition may also be added during the enzymatic hydrolysis. In case the enzymatic hydrolysis comprises a liquefaction step and saccharification step, additional enzymes may be added during and/or after the liquefaction step. The additional enzymes may be added before and/or during the saccharification step. Additional enzymes may also be added after the saccharification step.

In an embodiment the total enzymatic hydrolysis time is 10 hours or more, 12 hours or more, 14 hours or more, 16 hours or more, 18 hours or more, 20 hours or more, 30 hours or more, 40 hours or more, 50 hours or more, 60 hours or more, 70 hours or more, 80 hours or more, 90 hours or more, 100 hours or more, 110 hours or more, 120 hours or more, 130 hours or more, 140 hours or more, 150 hours or more, 160 hours or more, 170 hours or more, 180 hours or more, 190 hours or more, 200 hours or more.

In an embodiment, the total enzymatic hydrolysis time is 10 to 300 hours, 16 to 275 hours, preferably 20 to 250 hours, more preferably 30 to 200 hours, most preferably 40 to 150 hours.

In an embodiment oxygen is added during the enzymatic hydrolysis. In an embodiment oxygen is added during at least a part of the enzymatic hydrolysis. Oxygen can be added continuously or discontinuously during the enzymatic hydrolysis. In an embodiment oxygen is added one or more times during the enzymatic hydrolysis. In an embodiment oxygen may be added before the enzymatic hydrolysis, during the addition of carbohydrate material to a container used of enzymatic hydrolysis, during the addition of enzyme to a container used of enzymatic hydrolysis, during a part of the enzymatic hydrolysis, during the whole enzymatic hydrolysis or any combination thereof. Oxygen is added to the one or more containers used in the enzymatic hydrolysis.

Oxygen can be added in several forms. For example, oxygen can be added as oxygen gas, oxygen-enriched gas, such as oxygen-enriched air, or air. Examples how to add oxygen include, but are not limited to, addition of oxygen by means of sparging, electrolysis, chemical addition of oxygen, filling the one or more containers used in the enzymatic hydrolysis from the top (plunging the hydrolysate into the tank and consequently introducing oxygen into the hydrolysate) and addition of oxygen to the headspace of said one or more containers. When oxygen is added to the headspace of the container(s), sufficient oxygen necessary for the hydrolysis reaction may be supplied. In general, the amount of oxygen added to the container(s) can be controlled and/or varied. Restriction of the oxygen supplied is possible by adding only oxygen during part of the hydrolysis time in said container(s). Another option is adding oxygen at a low concentration, for example by using a mixture of air and recycled air (air leaving the container) or by "diluting" air with an inert gas. Increasing the amount of oxygen added can be achieved by addition of oxygen during longer periods of the hydrolysis time, by adding the oxygen at a higher concentration or by adding more air. Another way to control the oxygen concentration is to add an oxygen consumer and/or an oxygen generator. Oxygen can be introduced, for example blown, into the carbohydrate material present in the hydrolysis container(s). It can also be blown into the headspace of the container.

In an embodiment oxygen is added to the one or more containers used in the enzymatic hydrolysis before and/or during and/or after the addition of the carbohydrate material to said one or more containers. The oxygen may be introduced together with the carbohydrate material that enters the hydrolysis container(s). The oxygen may be introduced into the material stream that will enter the container(s) or with part of the container(s) contents that passes an external loop of the container(s).

In an embodiment the container(s) used in the enzymatic hydrolysis and/or the fermentation have a volume of at least 1 $m^3$. Preferably, the containers have a volume of at least 1 $m^3$, at least 2 $m^3$, at least 3 $m^3$, at least 4 $m^3$, at least 5 $m^3$, at least 6 $m^3$, at least 7 $m^3$, at least 8 $m^3$, at least 9 $m^3$, at least 10 $m^3$, at least 15 $m^3$, at least 20 $m^3$, at least 25 $m^3$, at least 30 $m^3$, at least 35 $m^3$, at least 40 $m^3$, at least 45 $m^3$, at least 50 $m^3$, at least 60 $m^3$, at least 70 $m^3$, at least 75 $m^3$, at least 80 $m^3$, at least 90 $m^3$, at least 100 $m^3$, at least 200 $m^3$, at least 300 $m^3$, at least 400 $m^3$, at least 500 $m^3$, at least 600 $m^3$, at least 700 m³, at least 800 m³, at least 900 m³, at least 1000 m³, at least 1500 m³, at least 2000 m³, at least 2500 m³. In general, the container(s) will be smaller than 3000 m³ or 5000 m³. In case several containers are used in the enzymatic hydrolysis, they may have the same volume, but also may have a different volume. In case the enzymatic hydrolysis comprises a separate liquefaction step and saccharification step, the container(s) used for the liquefaction step and the container(s) used for the saccharification step may have the same volume, but also may have a different volume.

In an embodiment the enzymatic hydrolysis is done at a temperature of 40-90° C., preferably 45-80° C., more preferably 55-65° C.

Carbohydrate material as used herein includes any starch and/or sucrose and/or cellulose containing material. Preferably, carbohydrate material as used herein includes lignocellulosic and/or hemicellulosic material. Carbohydrate material suitable for use in the processes as described herein includes biomass, e.g. virgin biomass and/or non-virgin biomass such as agricultural biomass, commercial organics, construction and demolition debris, municipal solid waste, waste paper and yard waste. Common forms of biomass include trees, shrubs and grasses, wheat, rye, oat, wheat straw, sugar cane, cane straw, sugar cane bagasse, switch grass, miscanthus, energy cane, cassava, molasse, barley, corn, corn stover, corn fiber, corn husks, corn cobs, canola stems, soybean stems, sweet sorghum, corn kernel including fiber from kernels, distillers dried grains (DDGS), products and by-products from milling of grains such as corn, wheat and barley (including wet milling and dry milling) often called "bran or fibre" as well as municipal solid waste, waste paper and yard waste. The biomass can also be, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet, sugar beet pulp, wheat midlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the aforementioned singularly or in any combination or mixture thereof.

In an embodiment the carbohydrate material is pretreated before and/or during the enzymatic hydrolysis. Pretreatment methods are known in the art and include, but are not limited to, heat, mechanical, chemical modification, biological modification and any combination thereof. Pretreatment is typically performed in order to enhance the accessibility of the lignocellulosic material to enzymatic hydrolysis and/or hydrolyse the hemicellulose and/or solubilize the hemicellulose and/or cellulose and/or lignin, in the lignocellulosic material. In an embodiment, the pretreatment comprises treating the lignocellulosic material with steam explosion, hot water treatment or treatment with dilute acid or dilute base. Examples of pretreatment methods include, but are not limited to, steam treatment (e.g. treatment at 100-260° C., at a pressure of 7-45 bar, at neutral pH, for 1-10 minutes), dilute acid treatment (e.g. treatment with 0.1-5% $H_2SO_4$ and/or $SO_2$ and/or $HNO_3$ and/or HCl, in presence or absence of steam, at 120-200° C., at a pressure of 2-15 bar, at acidic pH, for 2-30 minutes), organosolv treatment (e.g. treatment with 1-1.5% $H_2SO_4$ in presence of organic solvent and steam, at 160-200° C., at a pressure of 7-30 bar, at acidic pH, for 30-60 minutes), lime treatment (e.g. treatment with 0.1-2% NaOH/Ca(OH)$_2$ in the presence of water/steam at 60-160° C., at a pressure of 1-10 bar, at alkaline pH, for 60-4800 minutes), ARP treatment (e.g. treatment with 5-15% $NH_3$, at 150-180° C., at a pressure of 9-17 bar, at alkaline pH, for 10-90 minutes), AFEX treatment (e.g. treatment with >15% $NH_3$, at 60-140° C., at a pressure of 8-20 bar, at alkaline pH, for 5-30 minutes).

The carbohydrate material may be washed. In an embodiment the carbohydrate material may be washed after the pretreatment. The washing step may be used to remove water soluble compounds that may act as inhibitors for the fermentation and/or hydrolysis step. The washing step may be conducted in manner known to the skilled person. Next to washing, other detoxification methods do exist. The lignocellulosic material may also be detoxified by any (or any combination) of these methods which include, but are not limited to, solid/liquid separation, vacuum evaporation, extraction, adsorption, neutralization, overliming, addition of reducing agents, addition of detoxifying enzymes such as laccases or peroxidases, addition of microorganisms capable of detoxification of hydrolysates.

In an embodiment the hydrolysis step is conducted until 70% or more, 80% or more, 85% or more, 90% or more, 92% or more, 95% or more of available sugar in the carbohydrate material is released.

In an embodiment the dry matter content of the carbohydrate material in the enzymatic hydrolysis is from 10%-40% (w/w), 11%-35% (w/w), 12%-30% (w/w), 13%-29% (w/w), 14%-28% (w/w), 15%-27% (w/w), 16%-26% (w/w), 17%-25% (w/w).

As described above, the present invention also relates to a process for the preparation of a fermentation product from lignocellulosic material, comprising the steps of (a) performing a process for the preparation of a sugar product from carbohydrate material as described above, (b) fermenting the sugar product to produce a fermentation product; and (c) optionally, recovering the fermentation product.

In an embodiment the fermentation (i.e. step b) is performed in one or more containers. In an embodiment the fermentation is done by an alcohol producing microorganism to produce alcohol. In an embodiment the fermentation is done by an organic acid producing microorganism to produce an organic acid. The fermentation by an alcohol producing microorganism to produce alcohol can be done in the same container(s) wherein the enzymatic hydrolysis is performed. Alternatively, the fermentation by an alcohol producing microorganism to produce alcohol and the fermentation by an organic acid producing microorganism to produce an organic acid can be performed in one or more separate containers, but may also be done in one or more of the same containers.

In an embodiment the fermentation is done by a yeast. In an embodiment the alcohol producing microorganism and/or the organic acid producing microorganism is a yeast. In an embodiment the alcohol producing microorganism is able to ferment at least a C5 sugar and at least a C6 sugar. In an embodiment the organic acid producing microorganism is able to ferment at least a C6 sugar. In an embodiment the alcohol producing microorganism and the organic acid producing microorganism are different microorganisms. In another embodiment the alcohol producing microorganism and the organic acid producing microorganism are the same microorganism, i.e. the alcohol producing microorganism is also able to produce organic acid such as succinic acid.

Further described herein are fermentation processes in which a microorganism is used for the fermentation of a carbon source comprising sugar(s), e.g. glucose, L-arabinose and/or xylose. The carbon source may include any carbohydrate oligo- or polymer comprising L-arabinose, xylose or glucose units, such as e.g. lignocellulose, xylans, cellulose, starch, arabinan and the like. For release of xylose or glucose units from such carbohydrates, appropriate carbohydrases (such as xylanases, glucanases, amylases and the like) may be added to the fermentation medium or may be produced by the modified host cell. In the latter case, the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases. This, in turn, will prevent repression of systems required for metabolism and transport of non-glucose sugars such as xylose. In a preferred process the modified host cell ferments both the L-arabinose (optionally xylose) and glucose, preferably simultaneously in which case preferably a modified host cell is used which is insensitive to glucose repression to prevent diauxic growth. In addition to a source of L-arabinose, optionally xylose (and glucose) as carbon source, the fermentation medium will further comprise the appropriate ingredient required for growth of the modified host cell. Compositions of fermentation media for growth of microorganisms such as yeasts or filamentous fungi are well known in the art.

The fermentation time may be shorter than in conventional fermentation at the same conditions, wherein part of the enzymatic hydrolysis still has to take part during fermentation. In one embodiment, the fermentation time is 100 hours or less, 90 hours or less, 80 hours or less, 70 hours or less, or 60 hours or less, for a sugar composition of 50 g/l glucose and corresponding other sugars from the lignocellulosic material (e.g. 50 g/l xylose, 35 g/l L-arabinose and 10 g/l galactose). For more dilute sugar compositions, the fermentation time may correspondingly be reduced. In an embodiment the fermentation time of the ethanol production step is between 10 and 50 hours for ethanol made out of C6 sugars and between 20 and 100 hours for ethanol made out of C5 sugars. In an embodiment the fermentation time of the succinic acid production step is between 20 and 70 hours.

The fermentation process may be an aerobic or an anaerobic fermentation process. An anaerobic fermentation process is herein defined as a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many micro-organisms use pyruvate or one of its derivatives as an electron and hydrogen acceptor thereby regenerating $NAD^+$. Thus, in a preferred anaerobic fermentation process pyruvate is used as an electron (and hydrogen acceptor) and is reduced to fermentation products such as ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotic and a cephalosporin. In a preferred embodiment, the fermentation process is anaerobic. An anaerobic process is advantageous, since it is cheaper than aerobic processes: less special equipment is needed. Furthermore, anaerobic processes are expected to give a higher product yield than aerobic processes. Under aerobic conditions, usually the biomass yield is higher than under anaerobic conditions. As a consequence, usually under aerobic conditions, the expected product yield is lower than under anaerobic conditions.

In another embodiment, the fermentation process is under oxygen-limited conditions. More preferably, the fermentation process is aerobic and under oxygen-limited conditions. An oxygen-limited fermentation process is a process in which the oxygen consumption is limited by the oxygen transfer from the gas to the liquid. The degree of oxygen limitation is determined by the amount and composition of the ingoing gas flow as well as the actual mixing/mass transfer properties of the fermentation equipment used. Preferably, in a process under oxygen-limited conditions, the rate of oxygen consumption is at least 5.5, more preferably at least 6 and even more preferably at least 7 mmol/L/h.

In an embodiment the alcohol fermentation process is anaerobic, while the organic acid fermentation process is aerobic, but done under oxygen-limited conditions.

The fermentation process is preferably run at a temperature that is optimal for the microorganism used. Thus, for most yeasts or fungal cells, the fermentation process is performed at a temperature which is less than 42° C., preferably 38° C. or lower. For yeast or filamentous fungal host cells, the fermentation process is preferably performed at a temperature which is lower than 35, 33, 30 or 28° C. and at a temperature which is higher than 20, 22, or 25° C. In an embodiment the alcohol fermentation step and the organic acid fermentation step are performed between 25° C. and 35° C.

In an embodiment of the invention, the fermentations are conducted with a fermenting microorganism. In an embodiment of the invention, the alcohol (e.g. ethanol) fermentations of C5 sugars are conducted with a C5 fermenting microorganism. In an embodiment of the invention, the alcohol (e.g. ethanol) fermentations of C6 sugars are conducted with a C5 fermenting microorganism or a commercial C6 fermenting microorganism. Commercially available yeast suitable for ethanol production include, but are not limited to, BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In an embodiment propagation of the alcohol producing microorganism and/or the organic acid producing microorganism is performed in one or more propagation containers. After propagation, the alcohol producing microorganism and/or the organic acid producing microorganism may be added to one or more fermentation containers. Alternatively, the propagation of the alcohol producing microorganism and/or the organic acid producing microorganism is combined with the fermentation by the alcohol producing microorganism and/or the organic acid producing microorganism to produce alcohol and/or organic acid, respectively.

In an embodiment the alcohol producing microorganism is a microorganism that is able to ferment at least one C5 sugar. Preferably, it also is able to ferment at least one C6 sugar. In an embodiment the invention relates to a process for the preparation of ethanol from carbohydrate material, comprising the steps of (a) performing a process for the preparation of a sugar product from carbohydrate material as described above, (b) fermentation of the sugar product to produce ethanol, and (c) optionally, recovery of the ethanol.

The fermentation can be done with a microorganism that is able to ferment at least one C5 sugar.

In an embodiment the organic acid producing microorganism is a microorganism that is able to ferment at least one C6 sugar. In an embodiment the invention relates to a process for the preparation of an acid from lignocellulosic material, comprising the steps of (a) performing a process for the preparation of a sugar product from carbohydrate material as described above, (b) fermentation of the sugar product to produce the acid; and (c) optionally, recovery of the acid. The fermentation can be done with a microorganism that is able to ferment at least one C6 sugar.

The alcohol producing microorganisms may be a prokaryotic or eukaryotic organism. The microorganism used in the process may be a genetically engineered microorganism. Examples of suitable alcohol producing organisms are yeasts, for instance *Saccharomyces*, e.g. *Saccharomyces cerevisiae*, *Saccharomyces pastorianus* or *Saccharomyces uvarum*, *Hansenula*, *Issatchenkia*, e.g. *Issatchenkia orientalis*, *Pichia*, e.g. *Pichia stipites* or *Pichia pastoris*, *Kluyveromyces*, e.g. *Kluyveromyces fagilis*, *Candida*, e.g. *Candida pseudotropicalis* or *Candida acidothermophilum*, *Pachysolen*, e.g. *Pachysolen tannophilus* or bacteria, for instance *Lactobacillus*, e.g. *Lactobacillus lactis*, *Geobacillus*, *Zymomonas*, e.g. *Zymomonas mobilis*, *Clostridium*, e.g. *Clostridium phytofermentans*, *Escherichia*, e.g. *E. coli*, *Klebsiella*, e.g. *Klebsiella oxytoca*. In an embodiment the microorganism that is able to ferment at least one C5 sugar is a yeast. In an embodiment, the yeast belongs to the genus *Saccharomyces*, preferably of the species *Saccharomyces cerevisiae*. The yeast, e.g. *Saccharomyces cerevisiae*, used in the processes according to the present invention is capable of converting hexose (C6) sugars and pentose (C5) sugars. The yeast, e.g. *Saccharomyces cerevisiae*, used in the processes according to the present invention can anaerobically ferment at least one C6 sugar and at least one C5 sugar. For example, the yeast is capable of using L-arabinose and xylose in addition to glucose anaerobically. In an embodiment, the yeast is capable of converting L-arabinose into L-ribulose and/or xylulose 5-phosphate and/or into a desired fermentation product, for example into ethanol. Organisms, for example *Saccharomyces cerevisiae* strains, able to produce ethanol from L-arabinose may be produced by modifying a host yeast introducing the araA (L-arabinose isomerase), araB (L-ribuloglyoxalate) and araD (L-ribulose-5-P4-epimerase) genes from a suitable source. Such genes may be introduced into a host cell in order that it is capable of using arabinose. Such an approach is given is described in WO2003/095627. araA, araB and araD genes from *Lactobacillus plantarum* may be used and are disclosed in WO2008/041840. The araA gene from *Bacillus subtilis* and the araB and araD genes from *Escherichia coli* may be used and are disclosed in EP1499708. In another embodiment, araA, araB and araD genes may derived from of at least one of the genus *Clavibacter*, *Arthrobacter* and/or *Gramella*, in particular one of *Clavibacter michiganensis*, *Arthrobacter aurescens*, and/or *Gramella forsetii*, as disclosed in WO 2009011591. In an embodiment, the yeast may also comprise one or more copies of xylose isomerase gene and/or one or more copies of xylose reductase and/or xylitol dehydrogenase.

The yeast may comprise one or more genetic modifications to allow the yeast to ferment xylose. Examples of genetic modifications are introduction of one or more xylA-gene, XYL1 gene and XYL2 gene and/or XKS1-gene; deletion of the aldose reductase (GRE3) gene; overexpression of PPP-genes TAL1, TKL1, RPE1 and RKI1 to allow the increase of the flux through the pentose phosphate pathway in the cell. Examples of genetically engineered yeast are described in EP1468093 and/or WO2006/009434.

An example of a suitable commercial yeast is RN1016 that is a xylose and glucose fermenting *Saccharomyces cerevisiae* strain from DSM, the Netherlands.

In an embodiment, the fermentation process for the production of ethanol is anaerobic. Anaerobic has already been defined earlier herein. In another preferred embodiment, the fermentation process for the production of ethanol is aerobic. In another preferred embodiment, the fermentation process for the production of ethanol is under oxygen-limited conditions, more preferably aerobic and under oxygen-limited conditions. Oxygen-limited conditions have already been defined earlier herein.

Alternatively, to the fermentation processes described above, at least two distinct cells may be used, this means this process is a co-fermentation process. All preferred embodiments of the fermentation processes as described above are also preferred embodiments of this co-fermentation process: identity of the fermentation product, identity of source of L-arabinose and source of xylose, conditions of fermentation (aerobic or anaerobic conditions, oxygen-limited conditions, temperature at which the process is being carried out, productivity of ethanol, yield of ethanol).

The organic acid producing microorganisms may be a prokaryotic or eukaryotic organism. The microorganism used in the process may be a genetically engineered microorganism. Examples of suitable organic acid producing organisms are yeasts, for instance *Saccharomyces*, e.g. *Saccharomyces cerevisiae*; fungi for instance *Aspergillus* strains, such as *Aspergillus niger* and *Aspergillus fumigatus*, *Byssochlamys nivea*, *Lentinus degener*, *Paecilomyces varioti* and *Penicillium viniferum*; and bacteria, for instance *Anaerobiospirillum succiniciproducens*, *Actinobacillus succinogenes*, *Mannhei succiniciproducers* MBEL 55E, *Escherichia coli*, *Propionibacterium* species, *Pectinatus* sp., *Bacteroides* sp., such as *Bacteroides amylophilus*, *Ruminococcus flavefaciens*, *Prevotella ruminicola*, *Succcinimonas amylolytica*, *Succinivibrio dextrinisolvens*, *Wolinella succinogenes*, and *Cytophaga succinicans*. In an embodiment the organic acid producing microorganism that is able to ferment at least one C6 sugar is a yeast. In an embodiment, the yeast belongs to the genus *Saccharomyces*, preferably of the species *Saccharomyces cerevisiae*. The yeast, e.g. *Saccharomyces cerevisiae*, used in the production processes of organic acid according to the present invention is capable of converting hexose (C6) sugars. The yeast, e.g. *Saccharomyces cerevisiae*, used in the processes according to the present invention can anaerobically ferment at least one C6 sugar.

Fermentation products that may be produced by the processes of the invention can be any substance derived from fermentation. They include, but are not limited to, alcohol (such as arabinitol, butanol, ethanol, glycerol, methanol, 1,3-propanediol, sorbitol, and xylitol); organic acid (such as acetic acid, acetonic acid, adipic acid, ascorbic acid, acrylic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, maleic acid, malic acid, malonic acid, oxalic acid, oxaloacetic acid, propionic acid, succinic acid, and xylonic acid); ketones (such as acetone); amino acids (such as aspartic acid, glutamic acid, glycine, lysine, serine, tryptophan, and threonine); alkanes (such as pentane, hexane, heptane, octane, nonane, decane, undecane, and dodecane), cycloalkanes (such as cyclopentane, cyclohexane, cycloheptane, and cyclooctane), alkenes (such as pentene, hexene, heptene, and octene); and gases (such as methane, hydrogen ($H_2$), carbon dioxide ($CO_2$), and carbon monoxide (CO)). The fermentation product can also be a protein, a vitamin, a pharmaceutical, an animal feed supplement, a specialty chemical, a chemical feedstock, a plastic, a solvent, ethylene, an enzyme, such as a protease, a cellulase, an amylase, a glucanase, a lactase, a lipase, an lyase, an oxidoreductase, a transferase or a xylanase. In a preferred embodiment an organic acid and/or an alcohol is prepared in the fermentation processes of the present invention. In a preferred embodiment an acid and/or ethanol is prepared in the fermentation processes as described herein.

In an embodiment the alcohol, the organic acid, the enzyme composition, the enzyme producing microorganism, the alcohol producing microorganism and/or the organic acid producing microorganism are recovered. The processes as described herein may comprise recovery of all kinds of products made during the processes including fermentation products such as ethanol. A fermentation product may be separated from the fermentation broth in manner know to the skilled person. Examples of techniques for recovery include, but are not limited to, chromatography, electrophoretic procedures, differential solubility, distillation, or extraction. For each fermentation product the skilled person will thus be able to select a proper separation technique. For instance, ethanol may be separated from a yeast fermentation broth by distillation, for instance steam distillation/vacuum distillation in conventional way.

In an embodiment the processes of the invention also produce energy, heat, electricity and/or steam.

In an embodiment the waste obtained after purification/recovery of the fermentation product can be used in the production of electricity. Electricity can be made by incineration of such waste. The electricity can be used in any one of the steps of the processes according to the present invention.

The beneficial effects as described herein are found for several carbohydrate materials and therefore believed to be present for the hydrolysis of all kind of carbohydrate materials. The beneficial effects are found for several enzyme compositions and therefore believed to be present for all kind of enzyme compositions.

EXAMPLES

Example 1

Effect of Glucose on Beta-Glucosidase Activity in an Enzyme Composition

Beta-glucosidase activity was determined at 37° C. and pH 4.40 using para-nitrophenyl-β-D-glucopyranoside (pNP-BDG) as substrate. Enzymatic hydrolysis of pNP-β-D-glucopyranoside results in release of para-nitrophenol (pNP) and D-glucose. Quantitatively released para-nitrophenol, determined under alkaline conditions, is a measure for enzymatic activity. After 10 minutes of incubation, the reaction was stopped by adding 1M sodium carbonate and the absorbance was determined at a wavelength of 405 nm. Beta-glucosidase activity was calculated making use of the molar extinction coefficient of para-nitrophenol.

A para-nitrophenol calibration line was prepared as follows. First a 10 mM pNP stock solution in 100 mM acetate buffer pH 4.40, comprising 0.1% BSA, was made. Subsequently, dilutions of this pNP stock were made and concentrations of 0.25, 0.40, 0.67 and 1.25 mM were obtained. Next, a substrate solution was made of 5.0 mM pNP-BDG in a 100 mM acetate buffer pH 4.40. To 3 ml substrate solution, 200 µl of the pNP dilutions and 3 ml 1M sodium carbonate was added. The absorption of the calibration mixtures was measured at 405 nm with an acetate buffer 100 mM used as a blank measurement. The pNP content was calculated using standard calculation protocols known in the art, by plotting the $OD_{405}$ versus the concentration of the pNP calibration samples with known concentration, followed by the calculation of the concentration of the unknown enzyme composition samples using the equation generated from the calibration line.

Enzyme composition samples were diluted in weight corresponding to an activity between 1.7 and 3.3 units. To 3 ml substrate solution, preheated to 37° C., 200 µl of diluted sample solution was added. This was recorded as t=0. After 10.0 minutes, the reaction was stopped by adding 3 ml 1M sodium carbonate. The beta-glucosidase activity was expressed in units per gram enzyme composition sample. One unit, referred to as BG unit herein, is defined as the amount of enzyme that liberates one nanomol para-nitrophenol per second from para-nitrophenyl-beta-D-glucopyranoside under the defined assay conditions (pH=4.40, T=37° C.).

The effect of addition of sugar on the beta-glucosidase activity after 8 weeks of storage at room temperature is shown in the below example.

*Rasamsonia emersonii* enzyme composition (i.e. a whole fermentation broth comprising cellulase, hemicellulase and/or pectinase) was produced essentially as described in WO 2011/000949. A beta-glucosidase (shown as SEQ ID NO:2 in WO2012/000890) was added to the *Rasamsonia emersonii* enzyme composition, resulting in an enzyme composition with 7390 BG units/g enzyme composition. The obtained enzyme composition was subsequently mixed with different amounts of glucose to get final enzyme compositions with a concentration range of 19-272 g sugar/kg enzyme composition.

From each final enzyme composition, a sample was taken and stored at −20° C. until further analysis (referred to as t=0). Subsequently, the final enzyme compositions were stored at room temperature for 8 weeks after which again a sample was taken and stored at −20° C. until further analysis (referred to as t=8). Each sample was analysed for beta-glucosidase activity and the beta-glucosidase activity measured after 8 weeks (t=8) of storage was expressed as % of the beta-glucosidase activity measured at the start (t=0).

The results are shown in Table 1. The results clearly show that 96% or higher beta-glucosidase activity after 8 weeks of storage can be found in the enzyme compositions comprising 36-272 g sugar/kg enzyme composition.

Example 2

Effect of Sugar Mixtures on Beta-Glucosidase Activity in an Enzyme Composition

The experiment was essentially done as Example 1 with the exception that the obtained enzyme composition was subsequently mixed with different types of sugar and analysis of beta-glucosidase activity was done after storage for 14 weeks at room temperature.

The results are shown in Table 2. The results clearly show that beta-glucosidase activity after 14 weeks of storage is even further improved when sugar mixtures are used.

TABLE 1

The effect of different amounts of glucose on beta-glucosidase activity measured after 8 weeks of storage (t = 8) as compared to the beta-glucosidase activity present at the start (t = 0).

| Glucose/enzyme composition (g/kg) | Beta-glucosidase activity (at t = 8 expressed as % of t = 0) |
|---|---|
| 19 | 91 |
| 36 | 96 |
| 109 | 99 |
| 220 | 97 |
| 272 | 96 |

TABLE 2

The effect of different amounts of sugar mixtures on beta-glucosidase activity measured after 14 weeks of storage (t = 14) as compared to the beta-glucosidase activity present at the start (t = 0).

| Sugar used | Sugar/enzyme composition (g/kg) | Beta-glucosidase activity (at t = 14 expressed as % of t = 0) |
|---|---|---|
| Glucose | 109 | 92 |
| Glucose + lactose | 202 (108 + 94) | 93 |
| Glucose + lactose + xylose | 242 (108 + 94 + 40) | 97 |
| Glucose + xylose | 149 (110 + 39) | 94 |

The invention claimed is:

1. An enzyme composition comprising:
   a) a cellulase, a hemicellulase and/or a pectinase, and
   b) 148-244 g sugar/kg enzyme composition,
   wherein the enzyme composition comprises at least two types of sugar, and
   wherein the two types of sugar are: glucose and lactose; or glucose and xylose.

2. The enzyme composition according to claim 1, wherein the enzyme composition comprises a fungal cellulase, a fungal hemicellulase and/or a fungal pectinase.

3. The enzyme composition according to claim 1, wherein the composition comprises at least two cellulases and/or at least two hemicellulases.

4. The enzyme composition according to claim 1, wherein the enzyme composition comprises a cellulase, a hemicellulase and/or a pectinase selected from the group consisting of an endoglucanase, a beta-glucosidase, a lytic polysaccharide monooxygenase, a beta-xylosidase, an endoxylanase, a cellobiohydrolase and any combination thereof.

5. The enzyme composition according to claim 1, wherein the enzyme composition is a whole fermentation broth of a filamentous fungus.

6. The enzyme composition according to claim 1, wherein the composition has a pH of 2.0 to 5.5.

7. A kit comprising:
   a) a packaging, and
   b) the enzyme composition according to claim 1.

8. A process for preparation of a sugar product from carbohydrate material, comprising:
   a) enzymatically hydrolysing the carbohydrate material in one or more containers using the enzyme composition according to claim 1 or a kit comprising said composition to obtain a sugar product,
   b) optionally, recovering the sugar product.

9. A process for preparation of a fermentation product from carbohydrate material, comprising:
   a) performing the process according to claim 8,
   b) fermenting the sugar product to produce a fermentation product; and
   c) optionally, recovering the fermentation product.

10. The process according to claim 8, wherein the enzymatic hydrolysis comprises:
    a) a liquefaction wherein the carbohydrate material is liquefied in a first container to obtain liquefied material, and
    b) a saccharification wherein the liquefied material is hydrolysed in the first container and/or in a second container.

11. The process according to claim 8, wherein oxygen is added during the enzymatic hydrolysis.

12. The process according to claim 9, wherein the fermentation product is ethanol.

* * * * *